United States Patent [19]

Hartman

[11] Patent Number: 5,833,680
[45] Date of Patent: Nov. 10, 1998

[54] SANITARY NAPKIN

[76] Inventor: Christine Hartman, 4936 Oyster Barn Rd. NW., Olympia, Wash. 98502

[21] Appl. No.: 752,905

[22] Filed: Nov. 20, 1996

Related U.S. Application Data

[63] Continuation of Ser. No. 337,877, Nov. 14, 1994, abandoned.

[51] Int. Cl.⁶ ..................................................... A61F 13/15
[52] U.S. Cl. ......................................................... 604/385.1
[58] Field of Search ................................ 604/385.1, 378, 604/397, 358, 386, 387

[56] References Cited

U.S. PATENT DOCUMENTS

| | | | |
|---|---|---|---|
| 2,092,346 | 9/1937 | Arone | 128/284 |
| 2,331,355 | 10/1943 | Strongson | 128/290 |
| 3,905,372 | 9/1975 | Denkinger | 128/285 |
| 3,983,873 | 10/1976 | Hirschman | 128/285 |
| 4,673,403 | 6/1987 | Lassen et al. | 604/385 R |
| 4,846,824 | 7/1989 | Lassen et al. | 604/385.1 |
| 5,057,096 | 10/1991 | Faglione | 604/385.1 |
| 5,300,055 | 4/1994 | Buell | 604/385.1 |

FOREIGN PATENT DOCUMENTS 588689  5/1947  United Kingdom.

*Primary Examiner*—John G. Weiss
*Assistant Examiner*—David J. Cho
*Attorney, Agent, or Firm*—J. I. Bohan

[57] ABSTRACT

A sanitary napkin provided on its upper surface with a contoured labial and vaginal engagement element which acts to inhibit twisting or other dislocating movement of the napkin while being worn. In addition, an effective fluid seal is thereby achieved and maintained by the labial and vaginal engagement element to permit controlled movement of fluids to the napkin portion which is in fluid connection and integral to the labial and vaginal engagement element.

11 Claims, 3 Drawing Sheets

SANITARY NAPKIN

RELATED APPLICATION

This application is a continuation of the patent application Ser. No. 08/337,877 entitled "IMPROVED SANITARY NAPKIN" filed on Nov. 14, 1994 by inventor, Christine Hartman.

TECHNICAL FIELD

The present invention relates to the field of sanitary napkins for personal feminine hygiene for absorption of body fluids. More particularly, the present invention is directed to a sanitary napkin provided with a vaginal engagement element which acts to inhibit twisting or other dislocating movement of the sanitary device while being worn and also assures that fluids are directed to the napkin portion.

DESCRIPTION OF PRIOR ART

U.S. Pat. No. 2,092,346 discloses a napkin portion with a centrally located tampon portion. However, binding straps are sewn to the napkin portion which straps engage leg bands which tend to exert pulling lateral forces on the pad. As discussed below, the present invention relies on compressive lateral forces on the pad caused by the inner thighs, labia, and vaginal walls of the wearer to maintain proper engagement with the vaginal opening to resist twisting of the napkin portion.

A pad with an upwardly protruding portion is shown in U.S. Pat. No. 3,905,372 for partial vaginal engagement. However, this sanitary device is designed specifically for use with slight discharges and there is no napkin portion, only a pad small enough to be completely enclosed within the outer labia. The focus of that device is to a different function and is not intended to affect the movement of a napkin portion.

A labial pad is shown in U.S. Pat. No. 3,983,873 with substantially elongated upper portions designed to be contained within the interlabial space and, similar to the device above, has no napkin portion.

U.S. Pat. No. 5,057,096 discloses a vulval pad member which is removable from the upper surface of a conventional napkin portion. The device does not involve vaginal engagement to prevent twisting of the napkin portion. It is designed to readily disconnect from the napkin portion, whereas it is a primary objective of the present invention to have a solid physical connection between the integral napkin and the vertical element.

U.S. Pat. No. 4,846,824 relates to a labial sanitary pad which seeks to have only partial disposition within the labial vestibule. It does not envision vaginal engagement in order to inhibit twisting or other movement of the napkin portion.

All of the aforesaid prior art devices were designed to resolve specific problems different from that of the present invention and do not address, therefore, the features of the present invention.

SUMMARY OF THE INVENTION

One of the problems with sanitary napkins relates to the tendency for the napkin to not remain in a flattened position against the body, especially during normal daily activities involving the use of the legs such as standing, walking, lifting etc. Usually after a short time of such activity the leg action causes the napkin to rotate about its longitudinal axis or otherwise deform to defeat its intended purpose of controlled containment of fluid that would otherwise stain the garments of the wearer. To inhibit such unwanted movement various systems are currently in use. One approach is to provide the bottom surface of the napkin with adhesive strips that interfaced with the undergarment to inhibit the movement of the napkin. Another approach is to provide the napkin with "wings" which wrap around an undergarment such as panties. These approaches have had limited success since the undergarments, being typically made of thin fabric, do not possess sufficient rigidity to withstand the turning forces being experienced.

The sanitary device of the present invention is comprised of a napkin portion of elongated configuration made primarily from natural or synthetic, soft, absorbent fibers; projecting upwardly from the upper surface of the napkin portion is a vertical element which is contoured as hereinafter described to resist slippage or rotation of the napkin portion.

DESCRIPTION OF PREFERRED EMBODIMENTS

Figure 1:
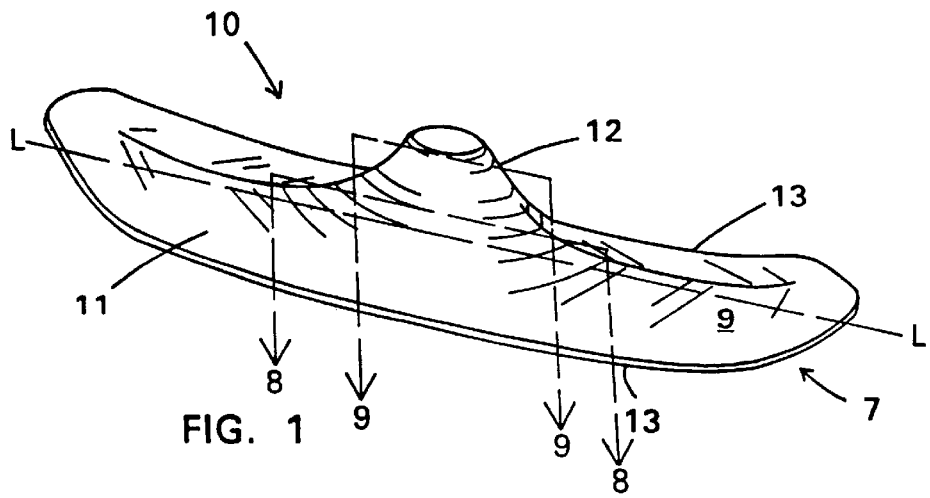
FIG. 1 is a perspective view of the sanitary napkin of the present invention with a centrally located vertical element.

The sanitary device 10 of the present invention has, as shown in FIG. 1, an elongated napkin portion 11 and a vertical element 12 extending from its upper surface. The napkin portion 11 has on its lower surface a fluid-impervious cover 7 (see FIG. 2), such as a polymeric film, which contacts the inside surface of undergarments of the wearer; today such undergarments are often panties, pantyhose or similar tight-fitting garments which aid in holding the sanitary device 10 to the wearer's body. The upper surface contacts the body of the wearer and has a protective sheath of fluid-permeable material 6 over all or a portion of the upper surface area.

Figure 8:
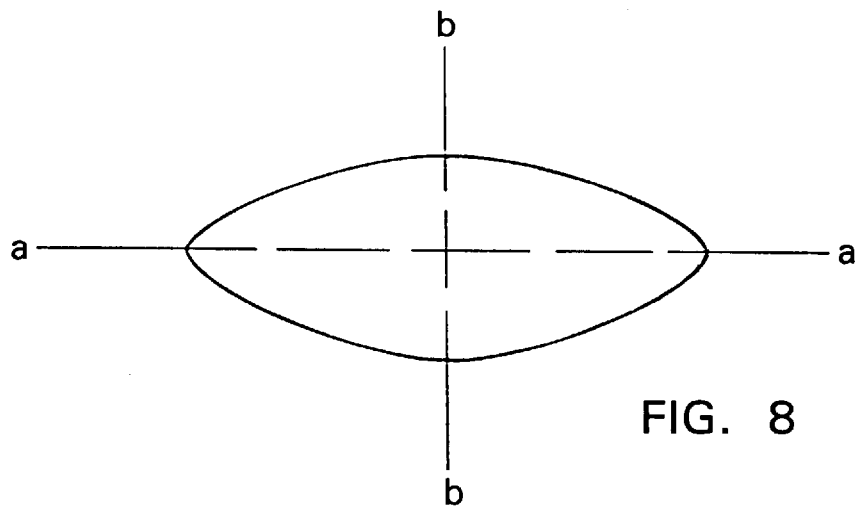
FIG. 8 is a cross-sectional view 8—8 near the base of the vertical element in FIG. 1.
Figure 9:
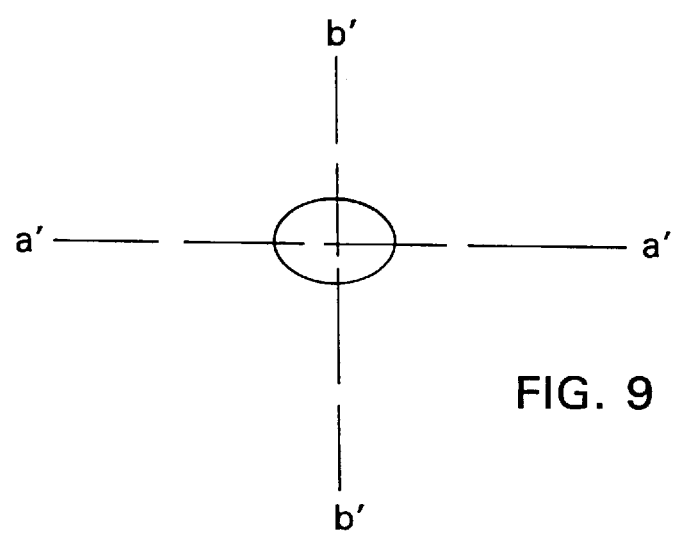
FIG. 9 is a cross-sectional view 9—9 near the upper terminus of vertical element in FIG. 1.

The vertical element 12 is integral to the upper surface of napkin portion 11 and is contoured such that it is oval or elliptical at the base where it interfaces with the vulval opening of the wearer; and the vertical element 12 gradually transitions to a generally cylindrical shape at its upper terminus at a point up to two inches or more but typically the preferred height is approximately 1.5 inches above the upper surface of napkin portion 11. FIG. 8 depicts the generally elliptical ross-section 8—8 of FIG. 1 of the vertical element near its base. As shown in FIG. 8 the length of major axis "a" is almost twice the length of the minor axis "b". The cross-section 9—9 of FIG. 1 (near, but somewhat below the upper terminus of the vertical element) is shown in FIG. 9; here the generally elliptical configuration has a major axis a' which is considerably shorter than the major axis "a" in FIG. 8. Moreover, the length of the major axis a' is less than one and one-half times the length of the minor axis b'. Further cross-sections of the vertical element above cross-section 9—9 would continue to be of an elliptical configuration, but with the relative length of the major axis coming ever closer in length to that of the minor axis until the two are substantially the same length at the upper terminus thus defining a generally circular configuration.

The transitional region intermediate to the elliptical and cylindrical regions of the vertical element 12 forms substantial contact with the interlabial space of the wearer. The vertical element 12 is designed so that the upper terminus engages the lower region of the vaginal cavity. In addition to providing an effective fluid seal about the full circumference of vertical element 12, this vaginal engagement inhibits rotational movement of the napkin portion 11. The vertical element 12 is provided with a core of absorbent material so that fluid readily travels to the napkin portion 11 by capillary or wicking action. By techniques well known in the art, the absorbent core of vertical element 12 and the absorbent material in napkin portion 11 can be of a uniform absorbent material or be multi-layered to control the transport and distribution of the fluids being absorbed.

When the sanitary device 10 of the present invention is in use, the inner thighs of the wearer contact the longitudinal perimeter 13 on both sides of napkin portion 11 causing it to be compressed inwardly, basically on a horizontal plane, during movement of the wearer, to conform to the individual's anatomy and in so doing causes the aforesaid oval regions in the lower portion of the vertical element 12 to conform to the interlabial space of the wearer. In this process, the cylindrical region in the upper portion of vertical element 12 conforms to the lower regions of the vaginal cavity to inhibit rotation of the napkin portion 11. There is an iterative effect since the napkin portion 11, being kept from turning or twisting, will continue to contact the thighs in a generally symmetrical manner which will exert inward, compressive forces on the sides 13 of napkin portion 11 to further encourage positioning of vertical element 12 in the labial and vaginal cavities.

The sanitary device of the present invention requires that the vertical element 12 and napkin portion 11 have sufficient structural interconnection that the anchoring effect of the vertical element 12 is adequately imparted to the napkin portion 11 to inhibit its tendency for lateral or twisting movement by means of rotation about its longitudinal axis (depicted in FIG. 1 as L—L) during walking and other physical activities of the wearer.

Figure 2:
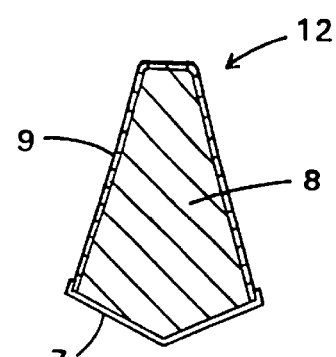
FIG. 2 is a cross-sectional view of the napkin of FIG. 1 through the vertical element.

One approach for effecting this interconnection is to provide the sanitary device 10 with an internal absorbing material 5 as shown in FIG. 2 with a substantially uniform matrix wherein the fibers running from the vertical element 12 to the napkin portion 11 impart the necessary physical interconnection. The fluid-absorbing material can be any of a wide variety of micro-porous webbings. A frequently used material is a webbing of polypropylene microfibers. For example, the fluid absorbing material 5 can be a homogeneous combination of thermoplastic, synthetic fibers and non-thermoplastic, natural or synthetic fibers well known in the art.

Blowing hot air through the inner matrix made of such combination will bond the thermoplastic synthetic fibers to the other fibers to impart structural interconnection between the vertical element 12 and the napkin portion 11. Another approach is to employ a multi-layered configuration well known in the art to control the transportation and distribution of fluids to the absorbing material where certain layers impart fluid absorbing properties and other layers impart fluid distribution or desired physical properties.

Another method of making the interconnection is to provide the upper surface of napkin portion 12 and the vertical element 12 with a conventional, fluid-permeable covering such as external webbing 6 as shown in FIG. 2. All or only portions of said upper surface can be covered with such netting 6 or other thin, permeable material which are commonly used for sanitary napkins. To effect the necessary resistance to rotation, the cover material, such as netting 6, will normally be needed at least on the vertical element 12 sides adjacent to the thighs of the wearer and the area of the napkin portion 11 just below the vertical element 12. The netting 6 or other cover material needs to have sufficient tensile strength, especially in the vicinity of vertical element 12, to maintain the physical integrity of the interconnection of element 12 with the napkin portion 11.

Figure 3:
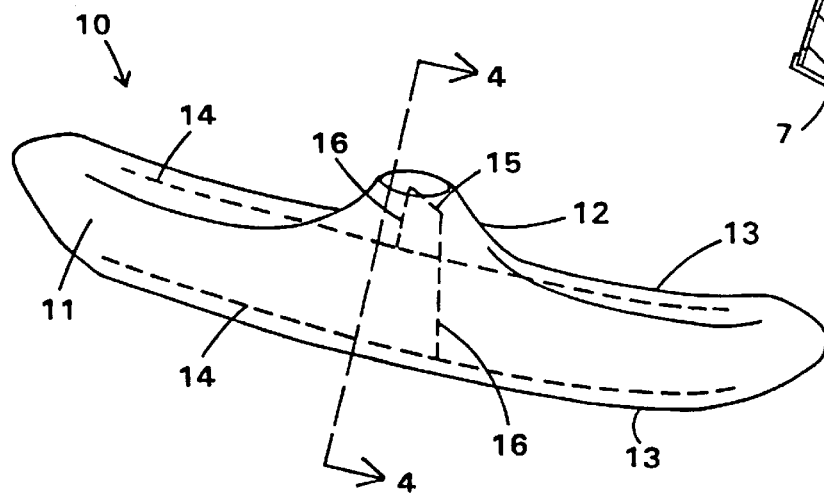
FIG. 3 is a perspective view of the sanitary napkin of the present invention depicting internal strengthening elements to inhibit rotation.
Figure 4:
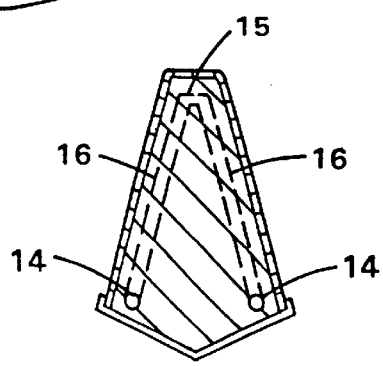
FIG. 4 is a cross-sectional view of the napkin of FIG. 3 through the vertical element.

In absorbing materials 5 which may have high absorption properties but low tensile or other physical properties, stiffening elements may be needed within the material matrix. As shown in FIG. 3 the anchoring effect of the vertical element 12 with the vaginal cavity can be imparted to the napkin portion 11 by providing reinforcement elements 14 and 15. In FIG. 4 vertical element 15 has two downwardly extending legs 16 which are integral to or affixed to elements 14 which extend longitudinally within napkin portion 11 slightly inward from and generally parallel to edges 13. Each leg 16 is affixed to element 14 by means of adhesives, thermal fusion, interlocking fibers or braiding and the like. Legs 16 and longitudinally-extending, reinforcing members 14 may be made from a wide variety of materials; for example comparatively rigid elements 14 and 15 may be made from twisted batting of either natural or synthetic materials which are lightly coated with liquid-impervious material such as plastic to minimize strength loss during prolonged use. Elements 14 and 15 may be comprised of plastic materials such as polyethylene or polystyrene or of a bundle of bonded thermoplastic fibers. It is preferable that the absorbing characteristics of elements 14 and 15 be limited so that their rigidity is not materially affected.

Figure 5:
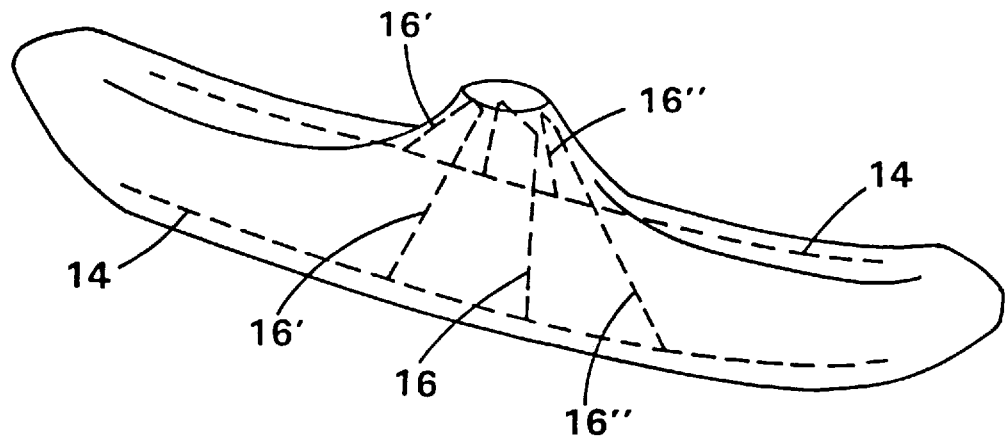
FIG. 5 is a cross-sectional view of the sanitary napkin of the present invention depicting the addition of further strengthening elements.
Figure 6:
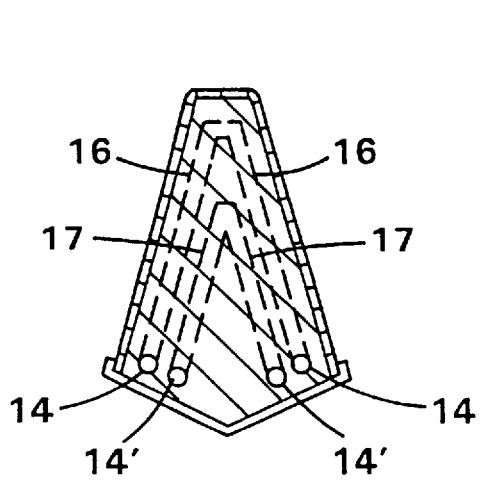
FIG. 6 is a cross-sectional view showing an alternative internal reinforcing configuration.

As shown in FIG. 5 a multiplicity of the vertical elements 16, 16' and 16" may be used to permit multiple strengthening connections to longitudinal element 14 to further enhance the rotational resistance of the sanitary device 10 of the present invention. Also a plurality of longitudinal reinforcement members 14 and 14' may be used as shown in FIG. 6 to interconnect with additional vertical members 17. Where the absorbing matrix includes, at least in part, thermoplastic fibers, application of heat to the fibers in the vicinity of the structural elements 14 and 15 will create a bond between the absorbent portion of the device and the shape-retaining elements 14 and 15 to inhibit rotation of the absorbing matrix portion of the napkin 11.

Figure 7:
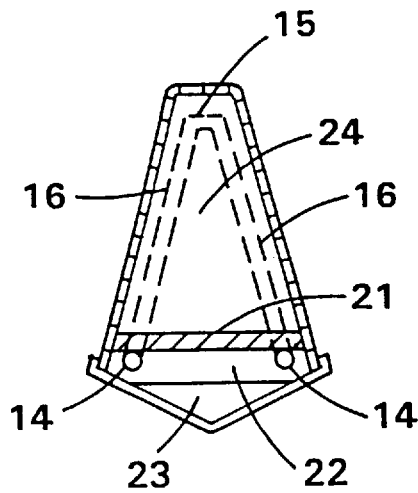
FIG. 7 is a cross-sectional view showing an absorbent napkin core comprised of multiple layers of absorbent material.

FIG. 7 shows an embodiment of the present invention where the absorbent core of the napkin portion is comprised of multiple layers 21, 22, 23 and 24 of absorbent material in order to provide controlled movement of fluids in accordance with methods well known in the art. When such multiple layers are preferred, the reinforcing effect of internal elements 14 are best served by providing layer 21 with material located above elements 14 having properties such that layer 21 will not be significantly compressed by upward pressure of element 14 when napkin portion 11 attempts to rotate downward on one side and exerts a downward pull on element 16 on that side; by so doing the integrity of the physical interconnection between vertical element 12 and napkin portion 11 is maintained and can, in fact, be enhanced by judicious selection of materials for layer 21.

The three approaches of providing interconnection between the vertical element 12 and the napkin portion 11 as described above by internal fiber strength, external netting or reinforcing elements are exemplary only; other approaches will become apparent to those skilled in the art. Moreover, one may combine two or all of these approaches to effect the needed physical interconnection.

Having thus described the invention, it is understood that one skilled in the art may accomplish the described results without departing from the spirit or scope of the following claims.

I claim:

1. A fluid-absorbing, sanitary device comprised of an elongated napkin portion extending along a longitudinal axis in a generally horizontal plane with a fluid-impervious lower surface, a fluid-absorbing core, and a fluid-permeable upper surface, said upper surface and fluid-absorbing core protruding upwardly from a centrally-located region of the napkin portion to form a vertical element portion with a vertical axis at generally a right angle to said horizontal plane for interfacing with the labial opening and lower regions of the vaginal cavity of the wearer, the napkin portion being of predetermined width and the vertical element protruding vertically to a predetermined height above the lower surface of the napkin portion to an upper terminus at its highest point of protrusion above the lower surface of the napkin portion, the vertical element portion being contoured such that in cross-section in the horizontal plane it generally defines an ellipse where it commences to protrude upwardly from the centrally-located region of the napkin portion such that a portion of the vertical element is capable of effecting a substantial interface and contact with the vulval opening of the wearer and the generally elliptical contour of the vertical element gradually transitions to a generally cylindrical shape in cross-section in the horizontal plane at its upper terminus so as to define a contoured upper surface along said gradual transition that is of a concave configuration for at least a portion of its upper surface associated with the vertical element whereby the vertical element at its highest point of protrusion is adapted to engage a portion of the vaginal cavity and during usage the predetermined width is compressed to a narrower width thus causing the vertical element to conform to the labial and lower vaginal cavities thereby inhibiting the lateral or rotational movement of the sanitary device.

2. A fluid-absorbing, sanitary device as in claim 1 wherein the fluid-absorbing core material in the napkin portion and the vertical element are comprised of a substantially-uniform, self-wicking, fluid-absorbent material.

3. A fluid-absorbing, sanitary device as in claim 2 wherein the substantially-uniform, self-wicking, fluid-absorbing core is comprised of a combination of thermoplastic, synthetic fibers and non-thermoplastic fibers which have been thermally treated to cause bonding of the thermoplastic fibers to each other as well as to adjacent non-thermoplastic fibers.

4. A fluid-absorbing, sanitary device as in claim 3 wherein the non-thermoplastic fibers are natural fibers.

5. A fluid-absorbing, sanitary device as in claim 3 wherein the non-thermoplastic fibers are synthetic fibers.

6. A fluid-absorbing, sanitary device as in claim 1 wherein the fluid-permeable upper surface on the vertical element and the adjacent upper surface areas of the napkin portion has sufficient tensile properties to maintain the physical integrity of the upper surface of the sanitary device.

7. A fluid-absorbing, sanitary device as in claim 6 wherein the fluid permeable upper surface is a netting material.

8. A fluid-absorbing, sanitary device as in claim 7 wherein the fluid permeable netting material is made from polyester fibers or rayon.

9. A fluid-absorbing, sanitary device as in claim 1 wherein the napkin portion contains a horizontally elongated, reinforcing member extending generally parallel to the longitudinal axis of the napkin portion that will impart longitudinal strength to said napkin portion and physically connected to each said elongated, reinforcing member is a vertically extending reinforcing member within the vertical element.

10. A fluid-absorbing, sanitary device as in claim 9 wherein each elongated, reinforcing member is physically connected to a vertically extending reinforcing member by adhesion, thermal fusion or mechanical means.

11. A fluid-absorbing, sanitary device as in claim 9 wherein the fluid-absorbing core of the napkin portion is comprised of at least two vertically disposed layers of microfibrous webbing wherein the layer of microfibrous webbing above the horizontal reinforcement members resists compression.

* * * * *